United States Patent [19]

Lennon et al.

[11] Patent Number: 5,256,540

[45] Date of Patent: Oct. 26, 1993

[54] IMMUNOASSAY FOR SMALL CELL LUNG CARCINOMA

[75] Inventors: Vanda A. Lennon, Rochester; Edward H. Lambert, Minneapolis; Thomas Kryzer; Guy E. Griesmann, both of Rochester, all of Minn.

[73] Assignee: Mayo Foundation for Medical Education and Research, Rochester, Minn.

[21] Appl. No.: 636,066

[22] Filed: Dec. 28, 1990

[51] Int. Cl.⁵ .................... C12Q 1/00; G01N 33/53; C07K 15/00
[52] U.S. Cl. .................... 435/7.23; 530/350
[58] Field of Search .................... 435/7.23; 424/85.9, 424/85.8

[56] References Cited

U.S. PATENT DOCUMENTS

| | | | |
|---|---|---|---|
| 4,514,506 | 4/1985 | Braatz et al. | 436/518 |
| 4,803,169 | 2/1989 | Tinsley et al. | 435/7 |
| 4,818,682 | 4/1989 | Linnane | 435/7 |
| 4,857,452 | 8/1989 | Ho | 435/7 |
| 4,863,851 | 9/1989 | McEwan et al. | 435/7 |
| 4,916,055 | 4/1990 | Yeoman et al. | 435/7 |
| 4,954,436 | 9/1990 | Froehner et al. | |

OTHER PUBLICATIONS

Lennon & Lambert 1989 Mayo Clin. Proc. 64:1498–1504.
Sher et al 1990 Cancer Res. 50: 3892–3896.
De Aizpurua et al. 1988 Annals NY Acad Sci. 540: 369–371.
H. J. DeAizpurua et al., Cancer Res. 48: 4719–4724 (1988).
V. A. Lennon et al., Mayo Clin. Proc. 64: 1498 (1989).
E. Sher et al., J. Autoimmunity 2: 909 (Abstract) (1989).
C. L. Williams et al., Soc. Neurosci. Abstr. 14: 66 (Abstract No. 30.1) (1988).
V. A. Lennon, Ann. Neurol. 28: 281 (abstract) (1990).
R. F. Burns et al., Anal. Biochem. 132:74 (1983).
E. Sher et al., The Lancet, Sep. 16, 1989 at pp. 640–643 (1989).
H. J. De Aizpurua et al., Annals NY Acad. Sciences 540: 369–371 (1988).
F. V. McCann et al., Science 212:1155–1157 (1981).
A. Roberts et al., Nature 317:737–739 (1985).
H. J. De Azipurua et al., Fed. Proc. 46:1380 (Abstract No. 6212) disclosed (1987).
J. J. Pancrazio et al., Cancer Res. 49:5901–5906 (1989).
H. J. DeAizpurua et al., Trans. Amer. Soc. Neurochem. 20: 221 (1989).

Primary Examiner—Robert J. Hill, Jr.
Assistant Examiner—K. Cochrane Carlson
Attorney, Agent, or Firm—Merchant, Gould, Smith, Edell, Welter & Schmidt

[57] ABSTRACT

An immunoassay for small cell lung carcinoma is provided which uses small cell lung carcinoma voltage-gated calcium channel antigen (SCC-VGCC Ag) comprising a detectable label and antibodies against SCC-VGCC Ag to detect endogenous SCC-VGCC Ag.

6 Claims, 1 Drawing Sheet

IMMUNOASSAY FOR SMALL CELL LUNG CARCINOMA

BACKGROUND OF THE INVENTION

Small cell lung carcinoma (SCC) is the prototype, and most lethal, of a group of tumors known as "APUDomas". These tumors express markers that are characteristic of neurons, including the $\gamma\gamma$ isozyme of enolase (known as "neuron-specific enolase", or NSE), the BB isozyme of creatine kinase and neuronal-type intermediate filaments. In addition, SCC is well known for secreting peptide hormones (e.g., ACTH, ADH) and growth factors (e.g., gastrin-releasing peptide, also known as "bombesin").

Over the years, several of these markers of SCC have been investigated for potential clinical applications. For example, products secreted or shed by SCC into a patient's serum, or expressed in tumor tissues, could be useful for tumor diagnosis, radionuclide imaging or therapeutic targeting of tumoricidal therapy. However, none of the SCC markers investigated to date has found wide clinical application. Therefore, there is a need to identify and isolate SCC factors which can be used in the diagnosis, imaging, monitoring and/or treatment of small cell lung carcinoma.

SUMMARY OF THE INVENTION

The present invention provides a diagnostic assay for small cell lung carcinoma (SCC) which is based on the detection of a new class of SCC antigen, hereinafter termed the "voltage-gated calcium channel [VGCC]antigen [Ag]of SCC" or "SCC-VGCC Ag". Preferably, the SCC-VGCC Ag in a physiological fluid of a human, preferably blood serum, is detected by an immunoassay, such as a competitive inhibition radioimmunoassay or a solid phase antigen capture assay.

The SCC-VGCC terminology is derived from the recognition that at least some epitopes on VGCC antigen may be common to both cholinergic neurons and the small cell carcinomas.

For example, in the neuromuscular disease, Lambert-Eaton myasthenic syndrome (LES), electrophysiologic and ultrastructural studies have implicated voltage-gated calcium channels (VGCC) of peripheral cholinergic nerve terminals as the target of pathogenic autoantibodies. Approximately 70% of LES patients have or will develop SCC. Recognition that SCC cells in culture exhibit VGCC activity, focussed attention on $\omega$-conotoxin-GVIA. This toxin, hereafter referred to as "$\omega$-CgTx," is a neurotoxin of the fish-eating snail *Conus geographus* that binds with high affinity to neuronal-type VGCC. It has been discussed as a potential tool for identifying an SCC component to which LES IgG might bind. H. J. DeAizpurua et al., *Trans. Amer. Soc. Neurochem.*, 20, 221 (1989) and *Cancer Res.*, 48, 4719 (1988).

The specific complexing of LES IgG antibodies with an $\omega$-CgTx-binding molecule extracted from SCC tumors was first demonstrated by V. A. Lennon et al., *Mayo Clin. Proc.*, 64, 1498 (1989) and was subsequently confirmed by E. Sher et al., *J. Autoimmunity*, 2, 909 (abstract) (1989) and *Cancer Res.*, 50, 3892 (1990). This phenomenon is the basis of a serological test that aids the diagnosis of LES (See V. A. Lennon et al., cited above).

Thus, the SCC-VGCC antigen is a new class of tumor antigen that has not been used or considered for use in the diagnosis of cancer. V. A. Lennon et al., op. cit., suggested that "if the complete molecular definition of the antigens...reveals that some epitopes are SCC-restricted, it should be feasible to design synthetic peptide vaccines to enhance a cytotoxic anti-tumor response". However, it has not been disclosed or suggested that $\omega$-CgTx in combination with SCC-VGCC antigen might be applied in an assay such as a modified competitive inhibition assay to detect and quantitate in human body fluids the SCC-VGCC antigen in a solubilized form (secreted or shed) as a diagnostic aid for SCC or other types of cancer.

Therefore, polyclonal or monoclonal antibodies which specifically bind to SCC-VGCC Ag can be used alone, or in combination with labelled SCC-VGCC Ag, to detect tumor antigens (or fragments thereof) in body fluids (e.g., serum, cerebrospinal fluid, ascites, pleural effusions and possibly urine) obtained from patients afflicted with small cell lung carcinoma and possibly, with related tumors (e.g., APUDomas, neuroblastoma). Testing of body fluids would be indicated clinically: 1) as a diagnostic test to initially screen for tumor antigens in persons at high risk for SCC (e.g., smokers with a family history of cancer) or in patients already suspected of having lung cancer; 2) to serially monitor, in the course of treatment (e.g., chemotherapy, X-irradiation), the disappearance of tumor antigen from serum; 3) as a periodic follow-up test, to detect tumor recurrence early.

BRIEF DESCRIPTION OF THE DRAWINGS

FIG. 1 is an SCC-VGCC-SCC Ag binding curve wherein the cpm ($\times 1000$) of labelled SCC-VGCC Ag are plotted against $\mu l$ of standard serum.

FIG. 2 is an SCC-VGCC Ag inhibition curve, wherein the percent inhibition of Anti-SCC-VGCC Ag binding to labelled SCC-VGCC Ag is plotted against fmol of unlabelled solubilized SCC-VGCC antibody (as tumor extract).

DETAILED DESCRIPTION OF THE INVENTION

In its broadest aspect, the present invention comprises using SCC-VGCC antigen which can incorporate a detectable label, or a binding site for a detectable label, in an immunoassay to detect endogenous SCC-VCGCC Ag in a physiological fluid, e.g., of a human such as a patient afflicted with SCC, or a human suspected of having SCC or related cancer.

SCC-VGCC Ag of a useful purity can be obtained from well-characterized SCC tumor lines by detergent extraction. The lines are derived from Mayo Clinic patients and established as continuous cell lines in culture and in athymic nude mice, in the Neuroimmunology Laboratory of the Mayo Clinic, Rochester, MN. The murine source of tumor can provide the quantities of antigen that are currently required for serologic testing. Recent studies indicate that normal human brain gray matter may be a satisfactory and more readily available alternative source of SCC-VGCC antigen. See C. L. Williams et al., *Soc. Neurosci. Abstr.*, 14, 66 (1988) and V. A. Lennon, *Ann. Neurol.*, 28, 281 (abstract) (1990).

To detect endogenous SCC-VGCC Ag in a sample by a competitive inhibition immunoassay, a known amount of anti-SCC-VGCC Ag antibody is added to a sample containing an unknown amount of endogenous SCC-VGCC Ag. The known amount is selected to be less than the amount required to complex all of the SCC-VGCC Ag suspected to be present, e.g., that would be present in a sample of the same amount of physiological fluid obtained from a patient known to have SCC. Next, a known amount of SCC-VGCC Ag comprising a detectable label is added. If endogenous SCC-VGCC Ag is present in the sample, no antibodies will be available to bind the labelled SCC-VGCC antigen, and it will remain free in solution. If no endogenous SCC-VGCC Ag is present, the added labelled SCC-VGCC antigen will complex with the added anti-SCC-VGCC antibodies to form binary complexes. Next, the binary antibody-antigen complexes are precipitated by an anti-human IgG antibody. The amount of radioactivity in the precipitate (a ternary complex) is inversely proportional to the amount of endogenous SCC-VGCC Ag that is present in the sample, e.g., a pellet free of radioactivity is indicative of the presence of endogenous SCC-VGCC Ag.

Presently, the most suitable source of the exogenous anti-SCC-VGCC antibodies is serum derived from selected LES patients (preferably non-smokers without evidence of cancer). Murine monoclonal anti-SCC-VGCC antibodies may also be useful in this assay.

Solid phase assays provide alternative systems for detecting SCC-VGCC antigens. For example, immobilized monoclonal anti-SCC-VGCC antibodies (rodent or human) e.g., bound to polystyrene plates or particles, can be used as tools for capturing soluble SCC-VGCC Ag. In a feasibility study, the capture of detergent-solubilized SCC-VGCC Ag by an immobilized rat anti-SCC-VGCC monoclonal antibody was demonstrated by the subsequent binding of $^{125}$I-$\omega$-CgTX. An immobilized irrelevant control rat monoclonal antibody did not capture solubilized SCC-VGCC Ag as judged by the insignificant binding of subsequently added $^{125}$I-$\omega$-CgTX. This is a prototype example of an alternative system that could be used to detect secreted or shed SCC-VGCC Ag in a patient's body fluids. The amount of SCC-VGCC Ag detected in a patient's body fluid sample in this assay is expressed in terms of moles of labelled probe, e.g., $^{125}$I-$\omega$-CgTX that specifically bind to the captured SCC-VGCC Ag, after the immobilized monoclonal anti-SCC-VGCC antibody is exposed to the patient's body fluid.

A second monoclonal anti-SCC-VGCC antibody can be used as an alternative probe to $^{125}$I-$\omega$-CgTX for detecting SCC-VGCC Ag captured by the immobilized monoclonal antibody. The second antibody can be labelled radioisotopically (e.g., by $^{125}$I) or conjugated directly to a detector enzyme (e.g., alkaline phosphatase or horse radish peroxidase), or can be labelled indirectly with a binding site for a detectable label, e.g., via biotinylation. The biotinylated antibody can then be detected by its ability to bind to an avidin-linked enzyme. If the second antibody is biotinylated, a detector enzyme conjugated to avidin will be subsequently added. The final step for detecting enzymes conjugated to monoclonal antibody or to avidin is the addition of a substrate appropriate for the enzyme to allow quantitative colorimetric detection of reaction product. The value (read in optical density units) is converted to fmol of SCC-VGCC Ag by reference to a standard curve generated in a control assay in which a standard extract of detergent-solubilized SCC-VGCC Ag is added in graded concentrations to the immobilized anti-SCC-VGCC monoclonal antibody.

A preferred method to label SCC-VGCC Ag is to react it with $\omega$-conotoxin-GVIA or "$\omega$-CgTx", which is available in a radiolabelled form that retains its high affinity for SCC-VGCC Ag (for example, $^{125}$I-labelled $\omega$-CgTx is available from Amersham Corp., Arlington Heights, Ill.). Complexes formed between radiolabelled $\omega$-CgTx and SCC-VGCC Ag retain their ability to bind to anti-SCC-VGCC Ag antibodies.

The invention will be further described by reference to the following detailed examples.

EXAMPLE 1

Preparation of SCC-VGCC Ag

SCC tumors (excised from athymic nude mice) or fresh human brain gray matter is used as a source of "detector" antigen, and for establishing a quantitative standard curve of immunoreactive units (fmol/ml). All steps are performed at 4° C. Tissues are chopped finely and dissociated in physiological phosphate-buffered saline by pushing the tissue through a stainless steel sieve (0.010 inch diameter wire, 40 mesh). After centrifugation at 850×g, the pelleted cells are transferred to a Teflonglass homogenizer in an equal volume of extraction buffer (20 mM Tris with 2% CHAPS, 20% glycerol, 0.02% NaN$_3$ and solid HEPES buffer to pH 7.5), with fresh protease inhibitors (PMSF, 10 $\mu$M; Pepstatin, 0.1 $\mu$g/ml; and aprotinin, 1 KIU/ml). After 5 manual strokes, the homogenate is shaken intermittently for 2 hr, and then ultracentrifuged at 100,000×g. Aliquots of the clear supernate are stored in plastic vials at −70° C. for use as SCC-VGCC antigen.

EXAMPLE 2

Labelling of Standard SCC-VGCC Extract With $^{125}$I-$\omega$-CgTX

The $^{125}$I-labelled $\omega$-CgTx (Amersham) is reconstituted in 1% acetic acid according to the supplier's instructions, and stored at −70° C. in polypropylene microcentrifuge tubes (Sarstedt, Princeton, N.J.) that are pretreated with 10% bovine serum albumen for 16 hr at 4° C. Immediately before use, the frozen toxin is thawed rapidly, neutralized (pH 7.4) with 1M NaOH, and added (221 fmol/ml) to a standard preparation of SCC-VGCC Ag prepared in accord with Example 1. After holding the mixture at 4° C. for 20 hr, unlabelled $\omega$-CgTx is added (20,000-fold molar excess) to prevent further binding of $^{125}$I-$\omega$-CgTX. SCC-VGCC Ag complexed with $^{125}$I-$\omega$-CgTX is now ready to use.

To determine nonspecific binding, a control extract of SCC tumor prepared as in Example 1, is preexposed for 1 hr to 20,000 fold molar excess of unlabelled $\omega$-CgTx before adding $^{125}$I-$\omega$-CgTx. Specific binding sites for $^{125}$I-$\omega$-CgTx are enumerated as the difference in radioactive ($\gamma$) counts in samples with and without unlabelled $\omega$-CgTx, determined by vacuum filtration on glass microtiter filters (Whatman, England) pretreated with 1% polyethylenimine in accord with the methodology of R. F. Bruns et al., *Anal. Biochem.*, 132, 74 (1983).

EXAMPLE 3

Establishment of an Antigen (SCC-VGCC Ag)-Binding Curve

Serial dilutions of a standard source of high affinity anti-SCC-VGCC Ag antibodies (currently 5$\mu$l or less of serum from a selected LES patient) are dispensed in duplicate siliconized glass tubes (10 by 75 mm; Baxter Scientific Products, McGraw Park, Ill.) containing 0.1 ml of assay buffer (40 mM sodium phosphate, 10 mM sodium chloride, 0.1% Tween 20, and 0.02% $NaN_3$). Normal human serum is added to make 5 μl the final volume of human serum.

The standard SCC-VGCC Ag extract complexed with $^{125}I$-ω-CgTX is admixed (17–40 pmol/l) with the antibody dilutions, and held at 4° C. for 16 hr. Anti-human IgG antibodies (e.g., from a goat hyperimmunized with human IgG and adjuvants) are added. After 30 min at 22° C., polyethylene glycol (PEG) is then added to a final concentration of 0.7% (to enhance the precipitation of immune complexes which, after 2 hr at 4° C., are pelleted by centrifuging for 5 min at 1750×g). The pelleted complexes are washed twice by repeated resuspension and recentrifugation in assay buffer containing 0.7% PEG. The pellets are counted for γ-emission with a gamma detector. The mean value for precipitates obtained from three tubes containing 5 μl of the normal human serum is subtracted from the value of each dilution of the anti-VGCC antiserum. The latter values are converted to moles of bound $^{125}I$-ω-CgTx by reference to the counts per minute for a daily standard of $^{125}I$-ω-CgTx (allowing for radioactive decay).

Figures 1, 2:
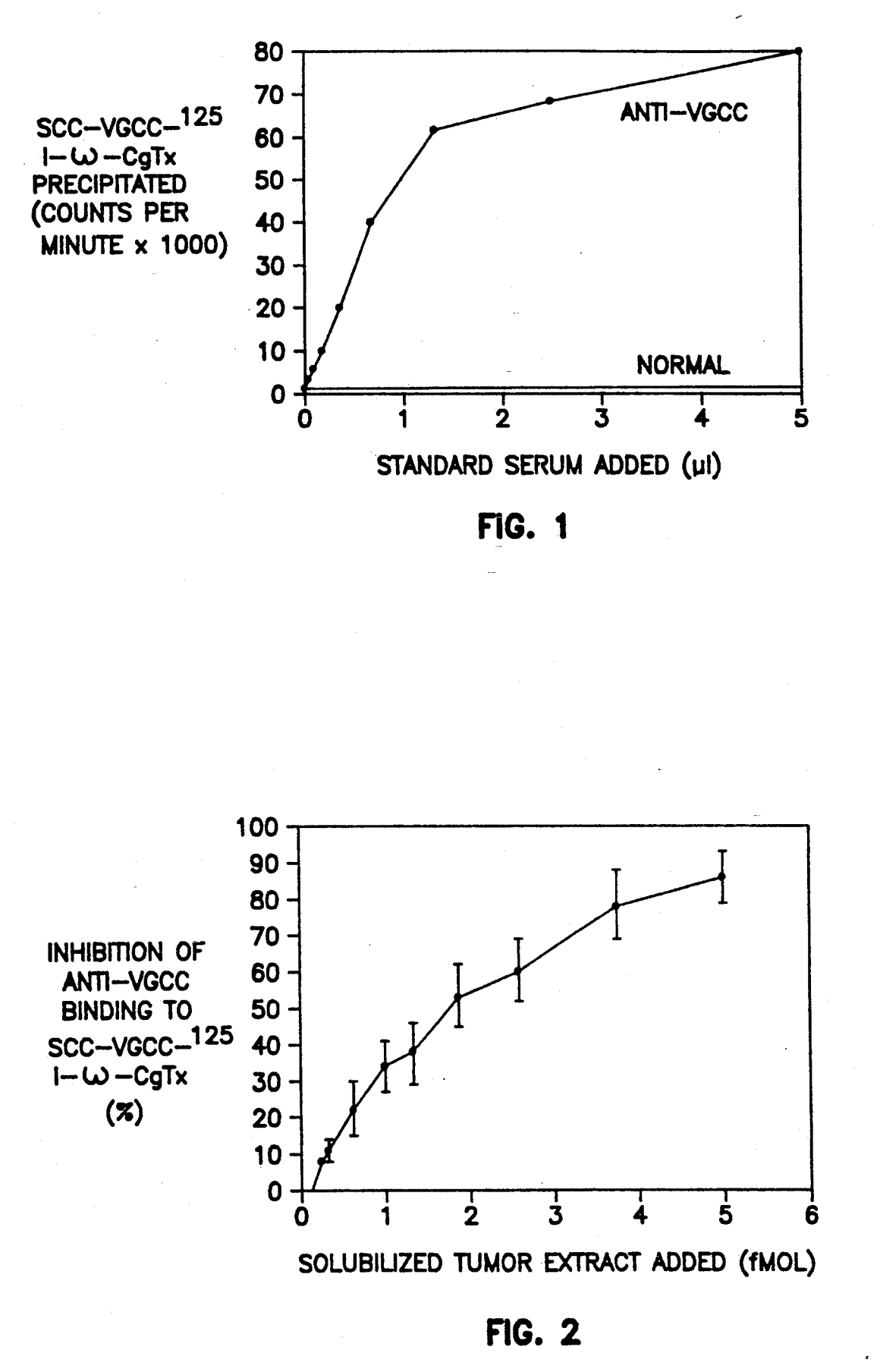

The dilution of anti-SCC-VGCC antiserum that precipitates 50% of the radioactive counts precipitated by undiluted (i.e., 5 μl) anti-SCC-VGCC antibodies is selected as the limiting dilution to be used in testing body fluids of patients with suspected cancer for the presence of immunoreactive SCC-VGCC Ag. A representative graph derived from these data is shown in FIG. 1.

EXAMPLE 4

Establishment of an Antigen (SCC-VGCC Ag)-Inhibition Curve

Graded quantities of SCC-VGCC Ag extract (currently 0.1 through 10.0 fmoles) complexed with an excess of unlabelled ω-CgTx (442 pmol/ml for 1 hr at 4° C. before use) are dispensed into duplicate siliconized glass tubes. Extraction buffer containing bovine serum albumin (30 mg/ml) is added to make the final volume 200 μl. A limiting dilution of the standard anti-SCC-VGCC Ag antiserum (with normal human serum to make a final solution of 5 μl human serum) is added in a final volume of 100 μl with assay buffer. The samples are held for 4 hr at 4° C. (to allow interaction of anti-SCC-VGCC Ag antibodies with immunoreactive fragments in the ω-CgTx-SCC-VGCC Ag extract). Next the standard SCC-VGCC Ag complexed with $^{125}I$-ω-CgTx is added for 16 hr at 4° C. Anti-human IgG antibodies (prepared in a goat) are added for 30 min at 22° C. Polyethylene glycol is then added to a final concentration of 0.7%.

After 2 hr at 4° C., antigen-antibody complexes are pelleted by centrifugation and washed twice by repeated resuspension and recentrifugation in assay buffer containing 0.7% PEG. The pellets are counted for γ-emission with a gamma detector. The mean value for precipitates obtained from three tubes containing 5 μl of normal human serum is subtracted from the value of each sample tested. The latter values are used to establish a reference inhibition curve by plotting counts per minute of $^{125}I$-ω-CgTx-SCC-VGCC Ag precipitated vs. moles of ω-CgTx-SCC-VGCC Ag [unlabelled] added per tube. A representative graph derived from these data is shown in FIG. 2.

EXAMPLE 5

Competitive Inhibition Radioimmunoassay For Detecting SCC-VGCC Ag in Serum

Fresh or deep frozen human blood serum is the most useful specimen to test. In a patient with a large burden of SCC tumor, soluble immunoreactive SCC-VGCC Ag can be detected in 10 μl of serum. However, with unknown samples it is preferred to use about 0.5 ml of serum. Protease inhibitors are added to the sample of serum (final concentration 0.01 mM PMSF, 0.1 μl ml Pepstatin A, 1 KIU/ml Aprotinin), which is then depleted of IgG by adding Sepharose beads conjugated with staphylococcal protein A and precoated with rabbit anti-human IgG. After 1 hr at 22° C. the beads are removed by centrifugation, and a limiting dilution of standard anti-SCC-VGCC Ag antiserum is added (e.g., 1 μl), with normal human serum added to make a final solution containing the equivalent of 5 μl of human serum. The samples are held for 4 hr at 4° C. (to allow interaction of anti-SCC-VGCC Ag antibodies with any immunoreactive fragments in the patient's IgG-depleted serum).

Next, the standard SCC-VGCC Ag complexed with $^{125}I$-ω-CgTx is added for 16 hr at 4° C. (together with 20,000 fold molar xs of nonradioactive ω-CgTx to prevent the $^{125}I$-ω-CgTx binding to putative SCC-VGCC Ag present in the patient's body fluid sample). Next, anti-human IgG antibodies are added for 30 min at 22° C. Polyethylene glycol is then added to a final concentration of 0.7%. After 2 hr at 4° C., antigen-antibody complexes are pelleted by centrifugation and washed twice by repeated resuspension and recentrifugation in assay buffer containing 0.7% PEG. The pellets are counted for γ-emission with a gamma detector. The mean value for precipitates obtained from three tubes containing 5 μl of normal human serum is subtracted from the value of each sample tested. The latter values are converted to moles per liter of SCC-VGCC Ag by reference to an inhibition curve such as that shown in FIG. 2.

EXAMPLE 6

Solid Phase Capture Assay for Detection and Quantification of SCC-VGCC Antigen in a Patient's Body Fluid Monoclonal IgG anti-SCC-VGCC antibodies (of rodent, human or chimeric murine-human hybridoma origin) are purified (e.g., by affinity chromatography on protein A-Sepharose) from tissue culture medium or from ascites fluids of athymic nude mice inoculated intraperitoneally with cells secreting the anti-SCC-VGCC antibodies. An anti-SCC-VGCC monoclonal IgG is coated directly onto a support substrate such as polystyrene beads or the wells of a plastic microtiter plate by conventional methodology. To increase the number of SCC-VGCC Ag capture sites, the monoclonal IgG can be biotinylated (by standard methodology). The support substrate in this case is precoated with a biotinylated linker protein (e.g., bovine serum albumin). After adding avidin to the plate coated with biotinylated linker protein, and washing, the biotinylated anti-SCC-VGCC monoclonal IgG is added. After 3 hr at 37° C. the monoclonal IgG solution is replaced by phosphate-buffered saline containing 0.05% Tween-20 and 10% normal goat serum ("wash buffer") for 1 hr at room temperature (to block residual non-specific protein-binding sites). The support substrate coated with anti-SCC-VGCC IgG (directly or via biotin-avidin-biotin linkage) is now ready to specifically capture SCC-VGCC antigen that might be present in a patient's body fluid.

The patient's body fluid sample (e.g., 200 μl of serum) is brought into contact with the anti-SCC-VGCC antibody-coated solid phase substrate (with protease inhibitors) for 1 hr at 22° C. followed by 16 hr at 4° C. Next the substrate is washed three times with "wash buffer". At this stage, a labelled probe is added to detect (and quantitate) any SCC-VGCC antigen complexed by the immobilized monoclonal IgG (in a binary complex). This can be done by adding a predetermined excess amount of $^{125}$I-ω-CgTx at pH 7.4 in phosphate-buffered saline containing 0.05% Tween-20, 2% normal goat serum and 200 μg/ml lysozyme (to prevent non-specific binding of the basically charged $^{125}$I-ω-CgTx). After 120 min at 22° C., and 16 hr at 4° C., the ternary complex bound to the plate is washed three times with phosphate-buffered saline containing 0.05% Tween-20, and the cpm of $^{125}$I-ω-CgTx bound to each well is counted by a gamma detector. After subtracting the means value for cpm of $^{125}$I-ω-CgTx bound to duplicate wells to which a control normal human serum sample has been added instead of a patient's serum, the corrected value (i.e, specific cpm) bound by the patient's sample is converted to the moles of bound $^{125}$I-ω-CgTx by reference to the cpm for a daily standard of $^{125}$I-ω-CgTx (allowing for radioactive decay).

An alternative to using $^{125}$I-ω-CgTx as the probe for detecting SCC-VGCC antigen captured from the patient's serum by the immobilized monoclonal anti-SCC-VGCC IgG, is to use a second monoclonal anti-SCC-VGCC antibody directed at a different epitope of the SCC-VGCC antigen. The second monoclonal antibody, labelled radioisotopically (e.g., $^{125}$I) or conjugated directly with enzyme (e.g., alkaline phosphatase or horse radish peroxidase), is allowed to bind for 45 min at 37° C. to form a ternary complex. After washing three times in phosphate buffered-saline containing 0.05% Tween-20, bound radioactivity is counted by a gamma detector. In the case of an enzyme-conjugated second antibody, an appropriate substrate is added to the ternary complex for 30 min at 37° C., and the reaction product is measured colorimetrically in terms of optical density units. This value is converted to fmol of SCC-VGCC antigen by reference to a standard curve generated in a control plate, in which, instead of a patient's body fluid, a standard extract of detergent-solubilized SCC-VGCC antigen was added in graded concentrations to the immobilized anti-VGCC monoclonal IgG.

All publications cited herein are incorporated by reference herein. The invention has been described with reference to various specific and preferred embodiments and techniques. However, it should be understood that many variations and modifications may be made while remaining within the spirit and scope of the invention.

What is claimed is:

1. A method for detecting small cell lung carcinoma voltage-gated calcium channel antigen (SCC-VGCC antigen) in a sample of a human physiological fluid comprising:
   (a) adding a preselected amount of an antibody specific for SCC-VGCC antigen to said sample of a human physiological fluid;
   (b) adding a preselected amount of labelled SCC-VGCC antigen to said sample; so that steps (a) and (b) result in the formation of antigen-antibody complexes;
   (c) precipitating the antibody-antigen complexes present in said sample with anti-immunoglobulin; and
   (d) measuring the amount of label in said precipitate.

2. A method for detecting small cell lung carcinoma voltage-gated calcium channel antigen (SCC-VGCC antigen) in a sample of a human physiological fluid, comprising:
   (a) combining a sample of a human physiological fluid comprising SCC-VGCC antigen with a preselected amount of anti-SCC-VGCC antigen antibody to form first binary antigen-antibody complexes comprising at least a portion of said anti-SCC-VGCC antibody;
   (b) adding a preselected amount of a complex between radiolabelled ω-conotoxin-GVIA and SCC-VGCC antigen which is sufficient to form second binary antigen-antibody complexes with any uncomplexed anti-SCC-VGCC antigen antibody;
   (c) adding an amount of anti-immunoglobulin effective to precipitate said complexes; and
   (d) measuring the amount of radioactivity in said precipitate, wherein the amount of radioactivity in said precipitate is inversely proportional to the amount of SCC-VGCC antigen in said sample.

3. The method of claims 1 or 2 wherein said physiological fluid is blood serum.

4. The method of claims 1 or 2 wherein said physiological fluid is obtained from a human afflicted with small cell lung carcinoma.

5. The method of claims 1 or 2 wherein said ω-conotoxin-GVIA is radiolabelled with $^{125}$I.

6. The method of claim 2 wherein essentially all of said anti-SCC-VGCC antibodies form said first binary complex with said SCC-VGCC Ag in step (a).

* * * * *